United States Patent [19]

Barrington et al.

[11] 4,184,258
[45] Jan. 22, 1980

[54] POWDER BLOWER DEVICE

[75] Inventors: James E. Barrington, Woburn; David L. Williams, Reading; Charles J. Hitchcock, Cambridge; Thomas J. Mullins, Woburn, all of Mass.

[73] Assignee: The United States of America as represented by the Department of Health, Education and Welfare, Washington, D.C.

[21] Appl. No.: 873,704

[22] Filed: Jan. 30, 1978

[51] Int. Cl.² .............................................. A61C 17/00
[52] U.S. Cl. ...................................... 433/88; 128/266; 222/636
[58] Field of Search .................. 222/194, 361; 302/49; 32/58, 40

[56] References Cited
U.S. PATENT DOCUMENTS

| | | | |
|---|---|---|---|
| 1,471,621 | 10/1923 | McCord | 222/361 |
| 2,825,135 | 3/1958 | Tilden | 32/58 |
| 3,281,022 | 10/1966 | Jarnett | 222/194 |
| 3,797,709 | 3/1974 | Ivanouich | 222/194 |

*Primary Examiner*—Robert Peshock
*Attorney, Agent, or Firm*—Browdy and Neimark

[57] ABSTRACT

A device for blowing powder onto teeth, the device consisting of a handpiece in the form of a housing connected to a compressed air source and having a discharge nozzle member which can be inserted in a patient's mouth and can be directed towards the patient's teeth. The housing has a powder reservoir with a bottom supply duct. An apertured shuttle bar is reciprocably slidably mounted beneath said duct and has a metering hole registrable with said supply duct and then, by longitudinally moving the bar, with a discharge conduit arranged to receive compressed air from the source so as to discharge a metered amount of powder in said hole into the nozzle member for delivery to the patient's teeth.

10 Claims, 4 Drawing Figures

POWDER BLOWER DEVICE

FIELD OF THE INVENTION

This invention relates to powder insufflating devices and/or the coating of teeth; and more particularly it relates to a dental powder insufflator for blowing metered amounts of powdered material, e.g. therapeutic material, into a patient's mouth and/or onto the patient's teeth.

BACKGROUND OF THE INVENTION

In the treatment of dental or mouth problems there is a need for a convenient and accurate means for delivering selected amounts of powdered chemotherapeutic material, such as adhesive and microcapsules, or a fluoride salt containing powder, or other desired treatment materials, in predetermined repeated dosages to a patient's teeth, or in the form of a metered single dosage, with the ability to select the specific teeth to be treated.

Although insufflation devices for introducing medicinal powder into various body cavities are known, none of the previously known devices provides the ability to repeatedly furnish a desired number of accurately known dosages and to direct the dosages to a patient's teeth. Furthermore, the previously known insufflation devices are relatively cumbersome, are difficult to refill, are subject to frequent clogging, and cause excessive loss and wastage of the powdered medicinal material.

A preliminary search reveals the following prior U.S. Pat. Nos. which appear to illustrate the present state of the art:

Harris,—3,998,226
Lazisky,—2,800,673
Crain et al.,—1,934,793
Kark,—2,501,279
Davis,—2,570,774

SUMMARY OF THE INVENTION

Accordingly, an object of the present invention is to overcome the deficiencies in the prior art, such as mentioned above.

Another object is to provide for the improved blowing of powder onto teeth.

A further object of the invention is to provide a novel and improved apparatus for delivering a predetermined dosage of powdered material to a patient's teeth.

A still further object of the invention is to provide an improved insufflation device for blowing powder onto teeth, or for delivering medicinal powder to the mouth or other parts of the body, the device being simple in construction and compact in size, and providing accurate metering of the powder.

A still further object of the invention is to provide an improved device for blowing chemotherapeutic material onto a patient's teeth in accurately measured dosages, and for repeating such dosages as required, with the ability to direct the dosages of powdered material to specific teeth, the device being substantially self-clearing so as to minimize clogging, being easy to refill, and providing economical utilization of the powdered therapeutic material.

A still further object of the invention is to provide an improved insufflation device for blowing doses of chemotherapeutic powdered material onto a patient's teeth, or for delivering doses of other medicinal powdered material to other parts of the body, the device being inexpensive to manufacture, being easy to manipulate, and having a minimum number of moving parts.

A still further object of the invention is to provide an improved device for blowing predetermined dosages of medicinal powder or other powdered chemotherapeutic material onto a patient's teeth, the device providing accurately metered doses of the material by the use of an apertured slidable dosing bar reciprocably disposed between the bottom dispensing duct of a powder reservoir and an offset delivery conduit leading to a discharge nozzle, the conduit carrying a stream of pressurized air, the bar having a metering aperture registrable with the dispensing duct and being movable longitudinally to bring the powder-filled metering aperture into registry with the delivery conduit, thereby allowing repeated measured doses of powder material to be delivered to the air stream of the device, and preventing loss of the powdered material when the dosing bar is not reciprocated.

BRIEF DESCRIPTION OF THE DRAWINGS

Further objects and advantages of the invention will become apparent from the following description of possible specific embodiments, and from the accompanying drawings thereof, wherein.

Figure 1:
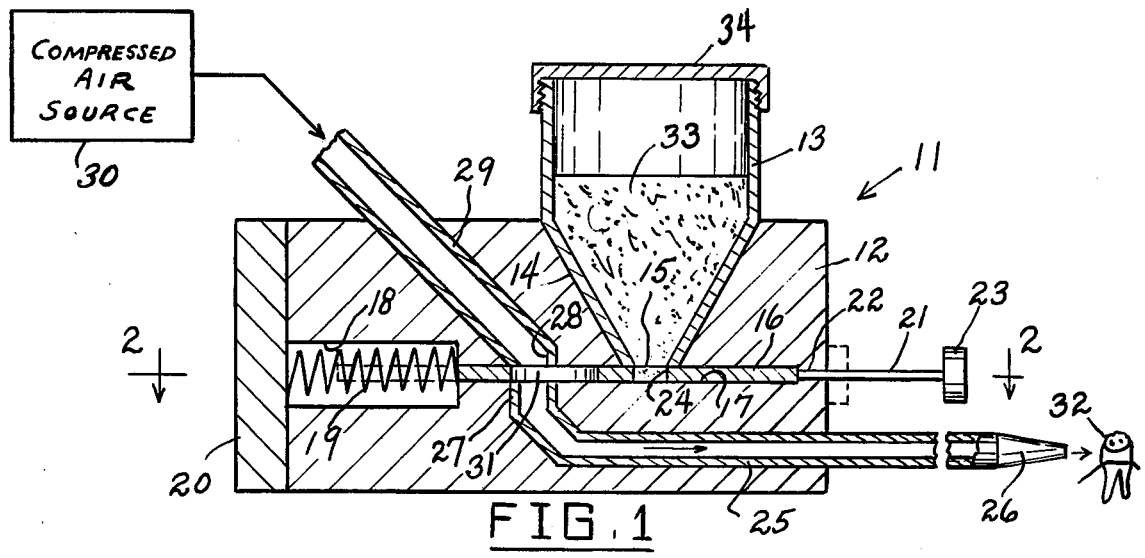
FIG. 1 is a longitudinal vertical cross-sectional view taken through one form of powder blower device constructed in accordance with the present invention.

It is to be understood that such embodiments are intended to be merely exemplary and in no way limitative.

DESCRIPTION OF PREFERRED EMBODIMENTS

Referring to the drawings, and more particularly to FIGS. 1 to 3, 11 generally designates a powder blower device according to the present invention. The device 11 comprises a handpiece consisting of an elongated housing 12 on which is mounted a powder storage hopper 13 having a downwardly tapering bottom portion 14 terminating in a discharge duct or orifice 15.

Designated at 16 is a shuttle bar which is slidably mounted in a longitudinal recesss 17 formed in housing 12 and extending subjacent duct 15. Housing 12 is formed at its forward portion with a bore 18 aligned with recess 17 and containing a coiled spring 19 which bears between housing end plate 20 and the left hand edge of bar 16, as viewed in FIG. 1, biasing bar 16 rightwardly toward the position shown in FIG. 1, namely, toward a rightward limiting position in recess 17.

Rigidly secured to the right end of bar 16, as viewed in FIG. 1, is a longitudinal rod element 21 extending slidably through a guide bore 22 in the right end portion of housing 12 and provided at its outer end with a push button or head 23 for exerting manual operating pressure on the dosage bar 16.

Bar 16 is formed with a dosage aperture 24 which registers with duct 15 in the normal position of bar 16, as shown in FIG. 1.

Secured in housing 12 is a longitudinally extending rigid discharge conduit 25 provided at its outer end with a powder blower nozzle element 26. Conduit 25 has an inner end portion 27 which extends perpendicular to and communicates with recess 17. Said conduit end portion 27 is aligned with the inner end 28 of an inclined air conduit 29 which is secured in housing 12 and which is connected to a compressed air source 30, which may comprise a compressor, blower, air bottle, or any other suitable regulated air pressure source.

Dosage bar 16 is formed with a longitudinal slot 31 which is located so that its left end portion, as viewed in FIG. 1, registers with and communicatively connects conduit portions 27 and 28 in the normal position of bar 16 shown in FIG. 1.

When button 23 is pushed leftwardly, as viewed in FIG. 1, the powder-filled dosage aperture 24 is moved leftwardly and can be brought into registry with the aligned conduit portions 27,28, whereby the dosage of powder is caught by the air stream through the conduit 25 and is discharged from the nozzle 26 toward its intended dental area, for example, a tooth 32 to be treated with the powder.

Figure 3:
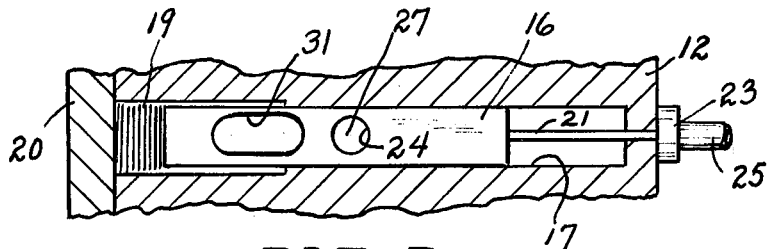
FIG. 3 is a fragmentary horizontal cross-sectional view of a portion of the structure of FIG. 2, but showing the dosage metering bar in a dosage-delivering position.

The rod 21 may be of suitable length to cause registry of aperture 24 with the aligned conduit portions 27,28 when button 23 engages the right end wall surface of housing 12, as shown in FIG. 3.

The elongated slot 31 allows the passage of air for nozzle cleaning purposes during inactive periods of use.

It will thus be seen that the powder blower device 11 can be employed to repeatedy deliver on demand consistent doses of a dry powder, dental therapeutic agent, or the like, shown at 33, to the teeth. For example, the therapeutic agent may comprise a microencapsulated cariostatic agent in an adhesive powder dispersion. The manually triggered device 11 transfers a predetermined dose volume of dental therapeutic agent 33 from the storage hopper 13 into the air stream conduit 25, which conveys the powder to the desired dental area via the aimed delivery nozzle 26, as above described. The transfer is accomplished by the reciprocating shuttle bar 16 containing the dosage metering cavity 24. In the inactivated mode the cavity 24 is aligned with the hopper orifice 15. When activated, the receiving cavity 24 is aligned with the delivering air stream conduit portions 27,28.

The hopper 13 retains the powder 33 in a dry form without spillage or compaction and is easily refilled. For example, the hopper 13 may have a screw cover cap 34 which can be removed for refilling the hopper; any other suitable refilling means may be employed, such as an attachable vial.

The powder storage hopper orifice delivers the stored powder 33 to the receiving cavity 15 of the shuttle bar 16, said cavity 15 performing two functions: (1) it determines the single dose volume of the powder agent to be delivered, and (2) it defines the receptacle wherein the powder is conveyed from the hopper orifice 15 to the air stream conduit elements 27,28.

The shuttle bar return spring 19 reciprocates the shuttle bar 16 when inactivated in order to realign the shuttle bar receiving cavity 24 with the hopper orifice 15 so that the next powder charge may enter the cavity 24.

Figure 2:
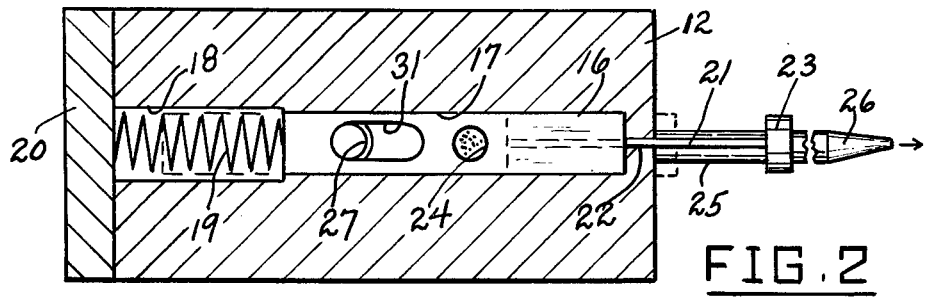
FIG. 2 is a horizontal cross-sectional view taken substantially on the line 2—2 of FIG. 1.

The recess 17 maintains the shuttle bar 16 in proper position in the housing 12 and restrains the shuttle bar from undesired movement relative to the hopper 13 and the air stream conduit elements 27,28. Also, the recess 17 has a sufficiently close fit with the shuttle bar 16 to prevent the powder from spilling during the transport from the hopper to the air stream. As seen in FIGS. 1 and 2, the housing 12 can be the support member for the delivery nozzle 26 and accessory components.

As above mentioned, when the device 11 is actuated the powder is introduced into the air stream and is conveyed to the delivery nozzle 26. Said nozzle 26 performs the following functions:

a. It is the instrument for aiming the powder at a specific dental area in need of therapy.

b. It restricts the size of the spray area.

c. It determines the position of the powder blower relative to the mouth and teeth.

d. It determines the ejection velocity of the air/powder suspension.

In operation, the air source 30 is activated, the powder blower hopper 13 is filled with the appropriate powder, and the nozzle 26 is held adjacent to the dental area to be treated. The shuttle bar control button 23 is actuated as above described to transfer the dose of powder from the hopper to the air stream, by which it is conveyed automatically via nozzle 26 to the selected dental area.

The air source 30 provides the compressed air conveyance for the powder, and the cleansing air for the shuttle bar 16 to prevent powder from jamming between the shuttle bar and the surfaces of recess 17.

Figure 4:
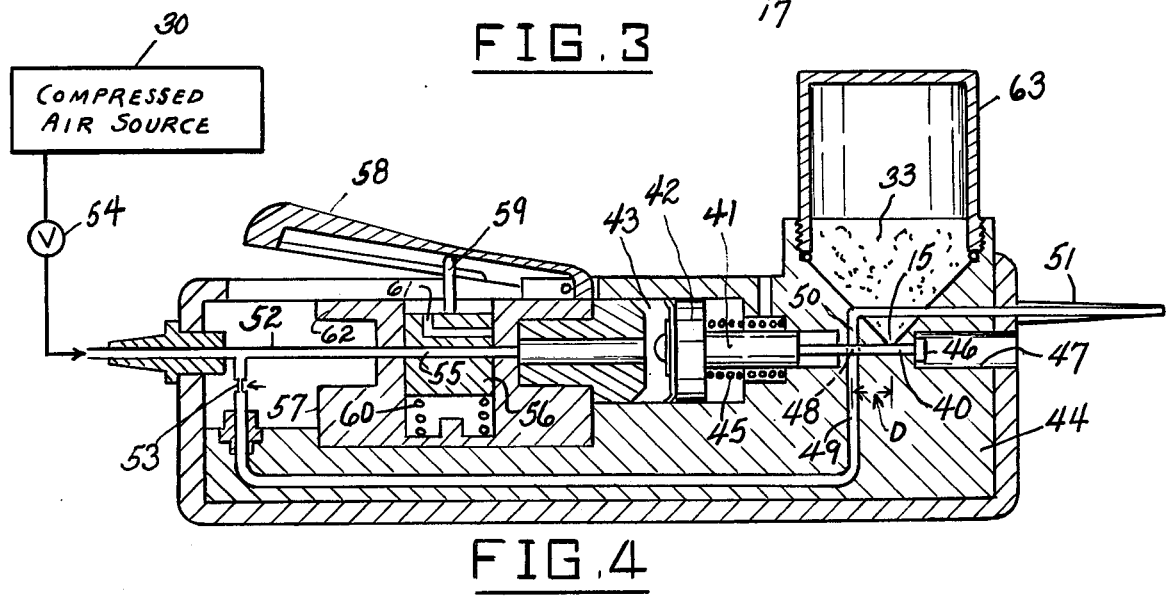
FIG. 4 is a longitudinal vertical cross-sectional view of a modified, semi-automatic form of powder blower device constructed according to the present invention.

FIG. 4 illustrates a semi-automatic form of powder blower according to the present invention wherein the compressed air source 30 is used to activate the shuttle bar via an integral piston. Thus, the shuttle bar, designated at 40, is integrally connected to the stem 41 of a piston 42 contained in a cylindrical bore 43 in the blower housing 44, and is biased leftward, as viewed in FIG. 4, by a coiled spring 45 surrounding the stem 41. The shuttle bar 40 has an end abutment head 46, movable in a recess 47 in housing 44, which limits the leftward travel of bar 40 to a blocking position relative to the hopper orifice 15. The shuttle bar 40 has a metering aperture 48 which is normally located in the air stream path defined between the aligned air conduit portions 49,50 leading to the powder delivery nozzle 51. The compressed air source 30 is connected to a main conduit 52 via a control valve 54, and the conduit portion 49 is connected to said main conduit 52 via an adjustable restriction 53. Main conduit 52 is normally connected to the bore 43 through the diametral passage 55 of the piston 56 of a control valve assembly 57 mounted in housing 44. The valve assembly 57 has an operating lever 58 engaging a piston pin 59 on valve piston 56, which is biased upwardly, as viewed in FIG. 4, by a coiled spring 60. Valve piston 56 has a vent passage 61 which is communicatively connected to bore 43 in place of passage 55 when lever 58 is rotated downwardly to a limiting position against the top flange 62 of valve assembly 57.

When control valve 54 is opened, compressed air through passage 55 acts on piston 42 and moves shuttle bar 40 rightwardly a distance D to bring metering cavity 48 beneath hopper orifice 15, causing cavity 48 to receive a charge of powder 33. The operator then suitably positions the nozzle 51 adjacent to the dental area to be treated and exerts squeezing force on the handpiece, thereby rotating lever 58 to its limiting inward position. This moves valve piston 56 to a position which vents bore 43 and allows spring 45 to return piston 42 to normal position thereof shown in FIG. 4, wherein the powder-filled cavity 48 is returned to alignment position between conduit portions 49,50. The air stream from conduit portion 49 then carries the powder dose to the nozzle 51 for application to the dental area being treated. Release of the valve control lever 58 allows the piston 42 to return the shuttle bar 40 to charging position, for repeating the dosage if required.

Refilling of the hopper may be accomplished by replacing the powder vial 63, when the hopper is empty, with a new full vial. This is done with the handpiece in an inverted position as compared with the operating position thereof shown in FIG. 4.

While certain specific embodiments of improved powder blowing devices have been disclosed in the foregoing description, it will be understood that various modifications within the spirit of the invention may occur to those skilled in the art. Therefore it is intended that adaptations and modifications should and are intended to be comprehended within the meaning and range of equivalents of the disclosed embodiments.

What is claimed is:

1. A therapeutic air/powder suspension spraying device for dental treatments comprising a handpiece in the form of a housing, powder reservoir means to contain a dental treatment powder in dry form, said reservoir means being mounted on said housing and having a bottom discharge orifice, a shuttle bar slidably mounted in a close-fit manner in said housing subjacent said orifice, said shuttle bar having a metering aperture registrable with said orifice to receive a metered volume of dry powder, means biasing said shuttle bar in a first position, means to reciprocate said shuttle bar between said first position and a second position, means in said housing substantially sealing the metering aperture against leakage during the filling thereof and the reciprocatory movement of the shuttle bar, means to deliver pressurized air comprising an air delivery conduit means in said housing opening at one side of said shuttle bar, discharge conduit means in said housing opening at the opposite side of said shuttle bar in alignment with said air delivery conduit means, said air delivery and discharge conduit means being offset from the reservoir bottom discharge orifice but aligned with the reciprocatory path of movement of said metering aperture, a compressed air source connected to said air delivery conduit means, and powder-guiding nozzle means connected to said discharge conduit means to direct powder to the teeth, to restrict the size of the spray area and to control the ejection velocity of the air/powder suspension.

2. The powder blowing device of claim 1, and wherein said shuttle bar is provided with an additional aperture registrable with said air delivery and discharge conduit means when said metering aperture is in registry with said reservoir bottom discharge orifice.

3. The powder blowing device of claim 1, wherein said biasing means comprises spring means acting in opposition to said shuttle bar reciprocating means.

4. The powder blowing device of claim 3, and wherein said spring means biases said shuttle bar towards a position wherein said metering aperture is in registry with said reservoir bottom discharge orifice.

5. The powder blowing device of claim 3, and wherein said spring means biases said shuttle bar towards a position closing off said reservoir bottom discharge orifice.

6. The powder blowing device of claim 1, and wherein said powder-guiding nozzle means is rigidly connected to said housing.

7. The powder blowing device of claim 6, and wherein said housing is of elongated shape and said powder-guiding nozzle means is secured to one end of the housing.

8. The powder blowing device of claim 7, and wherein said nozzle means projects longitudinally from said one end of the housing.

9. The powder blowing device of claim 1, and wherein said means to reciprocate the shuttle bar comprises pneumatic means.

10. The powder blowing device of claim 9, and wherein said housing is of elongated shape and said means to reciprocate the shuttle bar comprises a spring-biased force-transmitting element connected to the shuttle bar and having a piston thereon reciprocable in a cylinder, conduit means to pass pressurized air to said cylinder against said piston, and valve means along said conduit to control the flow of pressurized air to said cylinder.

* * * * *